(12) United States Patent
Hoskins et al.

(10) Patent No.: US 8,236,972 B2
(45) Date of Patent: Aug. 7, 2012

(54) MOLECULAR MASS ENHANCEMENT OF BIOLOGICAL FEEDSTOCKS

(75) Inventors: Travis J. C. Hoskins, Atlanta, GA (US);
Carsten Sievers, Atlanta, GA (US);
Pradeep K. Agrawal, Atlanta, GA (US);
Christopher W. Jones, Mableton, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 964 days.

(21) Appl. No.: 12/181,921

(22) Filed: Jul. 29, 2008

(65) Prior Publication Data

US 2010/0029926 A1    Feb. 4, 2010

(51) Int. Cl.
*C07D 307/42* (2006.01)
*C07D 307/48* (2006.01)
*C07D 307/50* (2006.01)
*C07D 307/54* (2006.01)

(52) U.S. Cl. ........ 549/488; 549/483; 549/491; 549/499; 549/500; 549/501

(58) Field of Classification Search .................. None
See application file for complete search history.

(56) References Cited

U.S. PATENT DOCUMENTS

| | | | |
|---|---|---|---|
| 4,417,088 A | 11/1983 | Miller | |
| 4,434,308 A | 2/1984 | Larkin et al. | |
| 4,827,064 A | 5/1989 | Wu | |
| 4,827,073 A | 5/1989 | Wu | |
| 4,990,709 A | 2/1991 | Wu | |
| 6,518,440 B2 * | 2/2003 | Lightner | 549/497 |
| 6,703,535 B2 | 3/2004 | Johnson et al. | |
| 7,850,841 B2 * | 12/2010 | Koivusalmi et al. | 208/64 |
| 7,880,049 B2 * | 2/2011 | Dumesic et al. | 585/733 |
| 2007/0135316 A1 * | 6/2007 | Koivusalmi et al. | 508/216 |

FOREIGN PATENT DOCUMENTS

WO    WO 2007/103858    9/2007

OTHER PUBLICATIONS

Lukevics et al., "Synthesis, psychotropic and anticancer activity of 2,2-dimethyl-5[5'-trialkylgermyl(silyl)-2'-hetarylidene]-1,3-dioxane-4,6-diones and their analogues" Applied Organometallic Chemistry (2003) vol. 17 pp. 898-905.*
Xu et al., "Study on the cis isomer of antischstosomal drug furapromide" Yaoxue Xuebao (1983) vol. 17 No. 12 pp. 905-908.*
Zhou et al., "Novel Synthesis of Nafronyl from Furfural" Zhongguo Yaowu Huaxue Zazhi (1997) vol. 7 No. 3 pp. 205-207.*
Huber et al., "Raney Ni-Sn Catalyst for H2 Production from Biomass-Derived Hydrocarbons . . . ", 300 Science (2003), pp. 2075-2077.
Huber et al., "Production of Liquid Alkanes by Aqueous-Phase Processing of Biomass-Derived Hydrocarbons", 308 Science (2005), pp. 1446-1450.
Barrett et al., "Single-reactor process for sequential aldol-condensation . . . ", 66 Appl. Catal. B-Environ (2006), pp. 111-118.
Chheda et al., "An overview of dehydration, aldol condensation and hydrogenation processes . . . ", 123 Catal. Today (2007), pp. 59-70.
Huber et al., "Renewable Alkanes by Aqueous-Phase Reforming of Biomass-Derived Oxygenates", 43 Angew. Chem.-Int. Edit. (2004), pp. 1549-1551.
Corma et al., "Determination of Base Properties of Hydrotalcites: Condensation of Benzaldehyde . . . ", 134 J. Catal. (1992), pp. 58-65.
Wiame et al., "Identification of the Basic Site on the Aluminovanadate Oxynitride Catalysts", 190 J. Catal. (2000), pp. 406-418.
Fripiat et al., "Role of nitrogen on the acid-base properties of zirconophosphate (ZrPON) . . . ", 181 Appl. Catal. A-Gen. (1999), pp. 331-346.
Corma et al., "Zeolites as Base Catalysts: Condensation of Aldehydes with Derivatives as Malonic Esters", 59 Appl. Catal. (1990), pp. 237-248.
Blanc et al., "The preparation and use of novel immoblised guanidine catalysts in base-catalysed epoxidation . . . ", 2 Green Chem. (2002), pp. 283-288.
Hagiwara et al., "Sequential Knoevenagel Reaction/Mislow—Evans Rearrangement Catalyzed by Heterogenous Amine . . . ", Synlett (2006), pp. 1601-1603.
Kantam et al., "Aldol & Knoevenagel condensations catalysed by modified Mg-Al hydrotalcite . . . ", Chem. Comm. (1998), pp. 1033-1034.
Ono, "Solid base catalysts for the synthesis of fine chemicals", 216 J. Catal. (2003), pp. 406-415.
Werpy et al., "Top Value Added Chemicals from Biomass . . . ", Rpt. No. NREL/TP-510-35523 (2004), at http://www.osti.gov/bridge.
Berkessel et al., "Chiral Chromium (III) Porphyrins as Highly Enantioselective Catalysts . . . ", 348 Adv. Synth. Catal. (2006), pp. 223-228.
Gilman et al. "Orientation in the Furan Series. IX. The Friedel-Crafts Reaction with 2-Furfural", 57 J. Am. Chem. Soc. (1935), pp. 906-907.

(Continued)

*Primary Examiner* — Eric S Olson
(74) *Attorney, Agent, or Firm* — Melissa Patangia; Christopher D. Northcutt; Gregory L. Porter

(57) ABSTRACT

The instant invention involves a process for enhancing molecular mass of biomass reactants. The process comprises first forming a substituted or unsubstituted furfural from a biomass. The substituted or unsubstituted furfural is then reacted with an activated methylene compound in the presence of a catalyst and, if desired, a solvent to form a Knoevenagel product. The product may then be hydrogenated to products containing an alcohol, ether, aldehyde, or ketone functional groups or to an olefinic or aliphatic species wherein as much as all of the oxygen and/or nitrogen has been removed.

27 Claims, 5 Drawing Sheets

OTHER PUBLICATIONS

MacQuerrie et al., "Organically modified hexagonal mesoporous silicas", 1 Green Chem. (1999), pp. 195-199.

Ragoussis, "Modified Knoevenagel Condensations. Synthesis of (E)-3-Alkenoic Acids", 28(1) Tetrahedron Lett. (1987), pp. 93-96.

Attanasi et al., "Effect of Metal Ions in Organic Synthesis. Part XVI. Knoevenagel Condensations . . . ", 13(14) Synth. Comm. (1983), pp. 1203-1208.

Ranu et al.,"Ionic Liquid as Catalyst and Reaction Medium—A Simple, Efficient and Green Procedure . . . ", Eur. J. Org. Chem. (2006), pp. 3767-3770.

Curini et al., "Potassium Exchanged Layered Zirconium Phosphate as Base Catalyst in Knoevenagel Condensation", 32 Synth. Comm. (2002), pp. 355-362.

Miller et al., "A Highly Catalytic and Selective Conversion of Carboxylic Acids to 1-Alkenes of One Less Carbon Atom", 58 J. Org. Chem. (1993), pp. 18-20.

Pollak, P. and Romeder, G. Malonic Acid and Derivatives (abstract). Kirk-Othmer Encyclopedia of Chemical Technology. (2000): Web. Aug. 5, 2011. <http://onlinelibrary.wiley.com>.

* cited by examiner

Synthesis of potential biofuels by Knoevenagel reaction and hydrodeoxygenation from 5-hydroxymethyl furfural Knoevenagel reactions between HMF/furfural and malonic acid Furfural: R = H
HMF: R=CH2OH $^1$H NMR spectrum of the unsaturated di-carboxylic acid formed between furfural and malonic acid via the Knoevenagel reaction.

Chemical shifts (300 MHz, DMSO) δ ppm: 7.83 (d, H1), 6.67 (dd, H2), 6.99 (d, H3), 7.3 (s, H4).

$^1$H NMR spectrum of the unsaturated mono-carboxylic acid formed between furfural and malonic acid via the Knoevenagel reaction.

Chemical shifts (300 MHz, DMSO) δ ppm: 7.83(d, H1), 6.62 (dd, H2), 6.92 (d, H3), 6.12 (d, H5), 7.36 (d, H4)

$^1$H NMR spectrum of the unsaturated di-carboxylic acid formed between HMF and malonic acid via the Knoevenagel reaction.

Chemical shifts (300 MHz, DMSO) δ ppm: 5.35 (s, H1), 4.38 (s, H2), 6.92 (d, H3), 6.46 (d, H4), 7.25 (s, H5)

$^1$H NMR spectrum of the unsaturated mono-carboxylic acid formed between HMF and malonic acid via the Knoevenagel reaction.

Chemical shifts (300 MHz) δ ppm: 4.32 (s, H1), 6.82 (d, H2), 6.41 (d, H3), 7.36 (d, H4), 6.12 (d, H5)

US 8,236,972 B2

MOLECULAR MASS ENHANCEMENT OF BIOLOGICAL FEEDSTOCKS

FIELD OF THE INVENTION

Provided herein is a process for enhancing molecular mass of biomass reactants. More specifically, the process involves preparing unsaturated organic compounds with one or more electron withdrawing groups from biomass-derived aldehydes or ketones such as furfurals. These compounds can then be further convened to branched hydrocarbons (e.g. alkanes or alkenes) by hydrodeoxygenation and/or hydrodenitrogenation to reduce unsaturation, oxygen, and/or nitrogen content.

BACKGROUND

In light of energy prices and environmental concerns, processes for the production of fuels from renewable feedstocks are needed. The most common process involves producing ethanol from corn. Unfortunately, using corn and the like as precursors competes with food and feed supplies.

Some processes employ lignocellulosic biomass as a feedstock because it is readily available and competitively priced. Lignocellulosic biomass often comprises polymeric carbohydrates (cellulose and hemicelluose), complex poly-aromatics (lignin), extractives and ashes and thereby does not compete with food and feed supplies.

WO 2007/103858, incorporated herein by reference, describes using biomass-derived carbohydrates to form alkanes. An aldol condensation of acetone with furfural or 5-hydroxymethyl furfural (HMF) followed by reduction of the coupled product in hydrogen gives alkanes having from approximately 8 to 18 carbon atoms. Unfortunately, the described process has numerous disadvantages. For example, the reactions often require a high strength base. Moreover, the low degree of branching of the derived alkanes also results in a low octane numbers which limit their use in izasoline. Therefore, the production of practical gasoline fuels from biomass using prior art methods requires additional processing steps adding to the cost and inefficiencies.

Accordingly, new processes are needed for use in making biofuels which are more efficient and more cost effective.

SUMMARY OF THE INVENTION

The instant invention provides new processes for use in making biofuels which are often efficient and may also be cost effective. In one embodiment, the instant invention relates to a process for enhancing molecular mass of biomass reactants comprising first forming a substituted or unsubstituted furfural from a biomass. Next, the substituted or unsubstituted furfural is reacted with an activated methylene compound comprising at least one electron withdrawing group in the presence of a catalyst. This results in the formation of a substituted or unsubstituted furan compound comprising one or more electron-withdrawing groups.

In another embodiment, the instant invention relates to a process for enhancing molecular mass of biomass reactants comprising first forming a substituted or unsubstituted aldehyde or ketone from a biomass. Next, the substituted or unsubstituted aldehyde or ketone is reacted with an activated methylene compound comprising at least one electron withdrawing group in the presence of a catalyst to form a substituted or unsubstituted Knoevenagel product. The substituted or unsubstituted Knoevenagel product is then reacted with $H_2$, or another reducing agent to form a hydrodeoxygenated and/or hydrodenitrogenated product.

BRIEF DESCRIPTION OF THE DRAWING FIGURES

DESCRIPTION OF EMBODIMENTS

Figure 1:
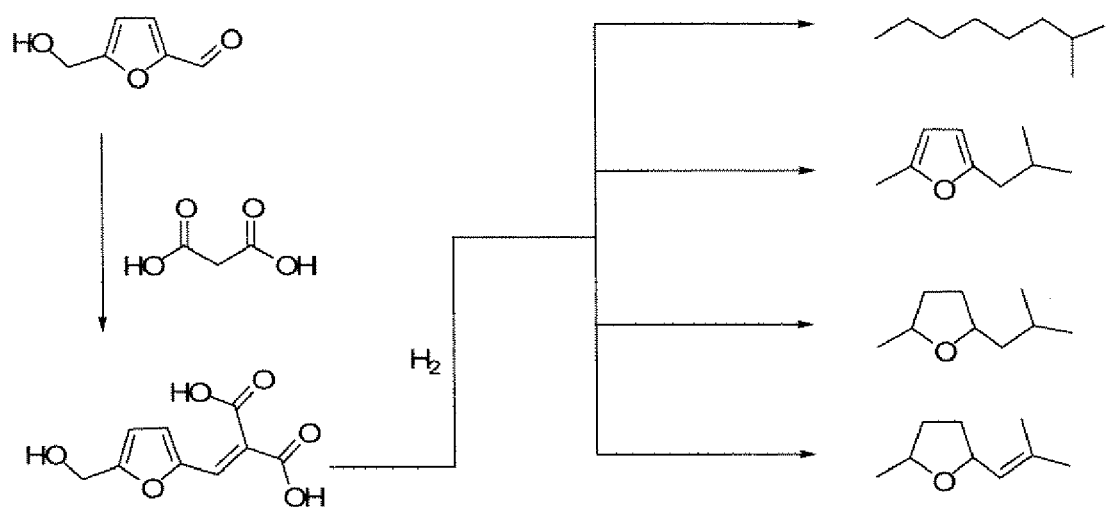
FIG. 1 is an illustration of one embodiment of the instant invention which comprises the synthesis of potential biofuels.
Figure 2:
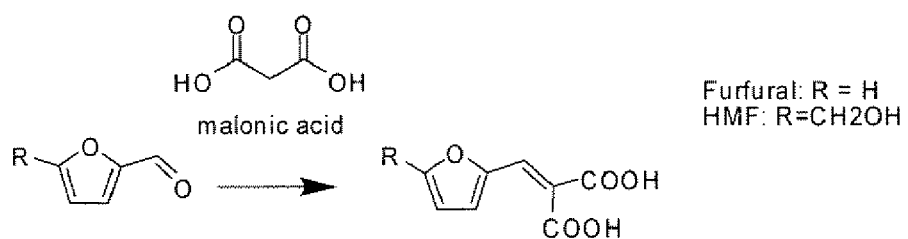
FIG. 2 is an illustration of another embodiment of the instant invention which comprises the synthesis of potential biofuels.

The instant invention relates to a process for enhancing molecular mass of biomass reactants. The process comprises first forming a substituted or unsubstituted aldehyde such as furfural, substituted or unsubstituted ketone, or mixture thereof from a biomass. The origin and type of the biomass employed is not particularly critical so long as it supplies the desired substituted or unsubstituted compound. A particularly preferable biomass is a lignocellulosic biomass, i.e., a plant biomass typically comprised of for example, cellulose, hemicellulose, poly(aromatics), such as lignin, extractives, ash, and mixtures thereof. Such lignocellulosic biomasses often comprise carbohydrate polymers (cellulose and hemicelluloses) tightly bound to the lignin, by hydrogen and covalent bonds. Biomass comes in many different types, which may be grouped into a few main categories: wood residues, including sawmill and paper mill discards, municipal paper waste, algae agricultural residues, including corn stover (stalks and straw), and sugarcane bagasse, and dedicated energy crops, which are mostly composed of fast growing tall, woody grasses.

Any of the aforementioned may find use in the instant invention. A particularly preferable biomass comprises one wherein greater than about 50, preferably greater than 60 weight percent of the biomass comprises carbohydrates.

The specific substituted or unsubstituted aldehyde, or ketone compound is not particularly critical so long as it is capable of being reacted with an activated methylene compound comprising at least one electron withdrawing group. i.e., a group capable of drawing electrons away from a reaction center, in the presence of a catalyst and, if desired, a solvent to form a Knoevenagel product.

Typical Knoevenagel reactants include substituted or unsubstituted aldehydes or ketones such as furan derivatives. The products typically include olefins and comprise one or more electron withdrawing groups and one or more carbon-carbon double bonds. Particularly preferable starting substituted or unsubstituted aldehyde or ketone compounds may be selected from the group consisting of substituted or unsubstituted aldehydes or ketones having from about five to about 9 carbon atoms. Suitable aldehydes or ketones include substituted or unsubstituted furfural, other bio-mass-derived aldehydes or ketones, as well as, mixtures thereof. Particularly preferable furfurals comprise unsubstituted furfural, 5-hydroxymethyl-furfural, and mixtures thereof.

The reaction between the substituted or unsubstituted aldehyde or ketone compound and activated methylene compound may occur in any convenient vessel, at any convenient temperature, and any convenient pressure. The reaction time, temperature, and pressure to be employed will vary depending upon the ingredients, desired products, and other reaction conditions. In this vein, closed pressure reactors or vessels equipped with condensers may be employed. Typically, while the reaction may be conducted at gentle reflux, the higher the temperature the faster the reaction will occur. Useful temperatures are often greater than about 50, preferably greater than about 60, preferably greater than 70, preferably greater than 75° C. Pressures typically range from atmospheric to elevated pressures generated autogenously in closed vessels.

The activated methylene compound employed may be any methylene compound capable of donating a proton when used with, for example, a basic catalyst. Useful activated methylene compounds may comprise a methylene group ($CH_2$) associated with one or two electron withdrawing groups such as carboxylic acids, ester or nitrile groups. Particularly preferable activated methylene compounds comprise substituted or unsubstituted malonic acid, its esters or derivatives thereof, as well as, malononitrile or a suitable derivative thereof, and substituted or unsubstituted levulinic acid, its esters or derivatives thereof. Suitable malonic acid esters may include any ester of malonic acid, preferably methyl and ethyl esters of malonic acid. Employing malonic acid as the activated methylene compound in a reaction with unsubstituted furfural, 5-hydroxymethyl-furfural, or mixtures thereof in the instant process usually results in Knoevenagel products comprising 2-((furan-2-yl)methylene)malonic acid, 2-((5-(hydroxymethyl)furan-2-yl)methylene)malonic acid, or a mixture thereof. Also, depending on the catalyst used, decarboxylation of the primary product may yield the following unsaturated mono-carboxylic acids: 3-(5-(hydroxymethyl)furan-2-yl)acrylic acid and 3-(furan-2-yl)acrylic acid.

The catalyst for the reaction between the substituted or unsubstituted aldehyde or ketone compound such as furfural and activated methylene compound varies depending upon, for example, the ingredients and reaction conditions. Typically, the catalyst comprises a base capable of extracting a proton from the activated methylene to form the desired substituted or unsubstituted Knoevenagel products or mixture thereof. Fortunately, such bases may often be of less strength than those required in, for example, aldol condensation. Bases with a strength ($pK_B$) of less than 6, preferably from about 3 to about 4 are often useful in the present invention. Typically, a suitable catalyst has a high surface area so that a high concentration of basic sites are exposed. Suitable catalysts include a catalyst selected from the group consisting of supported organic bases (e.g. ethylenediamine supported on poly(styrene), 3-aminopropyl-functionalized silica, dimethylaminopyridine on poly(styrene)), a solid base such as MgO, basic alumina, hydrotalcites, oxynitrides, alkali exchanged zeolites, and mixtures thereof.

Depending on the ingredients a solvent may be useful for the reaction between the substituted or unsubstituted aldehyde or ketone compounds and activated methylene compound. The specific solvent to be employed is usually not particularly critical so long as it is capable of significantly dissolving either the aldehyde or ketone or the activated methylene compounds. In some cases, one or both reactants can be used as solvents themselves. Thus, useful solvents may vary depending upon, for example, the ingredients and reaction conditions. Suitable solvents may include those selected from the group consisting of tetrahydrofuran (THF), ethyl acetate, diethyl ether, toluene, hexanes, water, isopropanol, and mixtures thereof.

Illustrative embodiments of the aforementioned process are described in FIGS. 1-6. Furthermore, as may be seen in the examples below, the typical yield of the aforementioned processes varies widely depending upon reactants, catalyst, and conditions. However, typically, a conversion of greater than 40, preferably greater than 50, more preferably greater than 60 percent based on aldehyde may be achieved. Particularly high conversion was exhibited in some of the examples below when ethylenediamine on polystyrene) or 3-aminopropyl-functionalized silica were used as catalysts. In contrast, the conversion in some of the specific examples below was less than 10%, for example when employing dimethylaminopyridine on poly(styrene) as a catalyst.

The substituted or unsubstituted Knoevenagel products formed in the aforementioned process may be further reacted to, for example, remove oxygen and/or nitrogen and form alkenes, alkanes, oxygenates or mixtures thereof which may be useful in or as fuels. Such further reactions processes may include, for example, hydrodeoxygenating and/or hydrodenitrogenating the substituted or unsubstituted Knoevenagel product to form a partially or fully reduced product. That is a hydrodeoxygenated product has at least one fewer oxygen atoms than the precursor Knoevenagel product, i.e., it is partially hydrodeoxygenated. Preferably, hydrodeoxygenated products have about 50% up to substantially all of the oxygen atoms removed, i.e., it is fully hydrodeoxygenated. Useful hydrodeoxygenating and hydrodenitrogenating steps are described in, for example, U.S. 20070135316 incorporated herein by reference. This may be readily accomplished by reacting the substituted or unsubstituted Knoevenagel product with $H_2$, or another reducing agent to form a product which is hydrodeoxygenated, hydrodenitrogenated, or both.

Advantageously, hydrodeoxygenated and/or hydrodenitrogenated products of the present invention are often characterized by one or more of the following characteristics: (1) a viscosity (as measured by ASTM D7042-04) of less than the substituted or unsubstituted Knovenagel product; (2) an energy density (as measured by ASTM D240-02) of greater than the substituted or unsubstituted Knovenagel product; or (3) a physical and/or chemical stability (as measured by ASTM D6468-06) of greater than the substituted or unsubstituted Knoevenagel product.

Often, depending upon the reaction and starting materials, the hydrodeoxygenated and/or hydrodenitrogenated products are advantageously comprised of a significant amount of substituted or unsubstituted branched alkenes or alkanes. Branched alkenes and alkanes are desirable because when fully hydrogenated branched alkenes and alkanes will usually have a higher octane rating than for fully hydrogenated n-alkenes and n-alkanes with the same molecular weight. Similarly, branched partially reduced products containing some oxygen generally have a higher octane rating than a corresponding straight chain partially reduced products containing substantially the same or the same oxygen-containing functional groups. Alkenes are particularly desirable because they often have a higher octane rating than alkanes. Moreover, the presence of the double bond in the ydrodeoxygenated and/or hydrodenitrogenated products allows for further increase of the molecular weight by dimerization or addition reactions. Further increasing the molecular weight through, for example, oligomerization, followed by hydrogenation to improve thermal and oxidative stability often makes the resulting compounds more useful in fuels such as diesel.

The oligomerization of olefins has been well reported in the literature, and a number of commercial processes are available. See, for example, U.S. Pat. Nos. 4,417,088; 4,434,308, 4,827,064; 4,827,073; 4,990,709; 6,703,535. Various types of reactor configurations may be employed, with the fixed catalyst bed reactor being used commercially. More recently, performing the oligomerization in an ionic liquids media has been proposed, since the contact between the catalyst and the reactants is efficient and the separation of the catalyst from the oligomerization products is facilitated. Preferably, the oligomerized product will have an average molecular weight at least 10 percent higher than the initial feedstock, more preferably at least 20 percent higher. The oligomerization reaction will proceed over a wide range of conditions. Typical temperatures for carrying out the reaction are between about 0° C. and about 425° C. Other conditions include a space velocity from 0.1 to 3 LHSV and a pressure from 0 to 2000 psig. Catalysts for the oligomerization reaction can be virtually any acidic material, such as, for example, zeolites, clays, resins $BF_3$ complexes, HF, $H_2SO_4$, $AlCl_3$, ionic liquids (preferably ionic liquids containing a Bronsted or Lewis acidic component or a combination of Bronsted and Lewis acid components), transition metal-based catalysts (such as $Cr/SiO_2$), superacids, and the like. In addition, non-acidic oligomerization catalysts including certain organometallic or transition metal oligomerization catalysts may be used, such as, for example, zirconocenes.

EXAMPLES

Example 1

A solution of 0.192 g furfural and 0.208 g malonic acid in 8 ml THF was prepared in a pressure tube and 25 mg 3-aminopropyl on silica on poly(styrene) was added as catalyst. The tube was placed in an oil bath that was heated to 70° C. After a reaction time of 13 h a conversion of 99% (aldehyde) was observed.

Example 2

A solution of 0.252 g HMF and 0.208 g malonic acid in 8 ml THF was prepared in a pressure tube and 25 mg 3-aminopropyl on silica was added as catalyst. The tube was placed in an oil bath that was heated to 70° C. After a reaction time of 24 h a conversion of 71% (aldehyde) was observed.

Example 3

A solution of 0.192 g furfural and 0.208 g malonic acid in 8 ml THF was prepared in a pressure tube and 10 mg dimethylaminopyridine on polystyrene was added as catalyst. The tube was placed in an oil bath that was heated to 70° C. After a reaction time of 13 h a conversion of 8% (aldehyde) was observed.

Example 4

A solution of 0.252 g HMF and 0.208 g malonic acid in 8 ml THF was prepared in a pressure tube and 25 mg 3-aminopropyl on silica was added as catalyst. The tube was placed in an oil bath that was heated to 70° C. After a reaction time of 13 h a conversion of 66% (aldehyde) was observed.

Example 5

A solution of 0.192 g furfural and 0.208 g malonic acid in 8 ml THF was prepared in a pressure tube and 12 mg ethylenediamine on poly(styrene) was added as catalyst. The tube was placed in an oil bath that was heated to 70° C. After a reaction time of 13 h a conversion of 49% (aldehyde) was observed.

Example 6

A solution of 0.252 g HMF and 0.208 g malonic acid in 8 ml THF was prepared in a pressure tube and 12 mg ethylenediamine on poly(styrene) was added as catalyst. The tube was placed in an oil bath that was heated to 70° C. After a reaction time of 13 h a conversion of 81±6% (aldehyde) was observed.

Example 7

A solution of 0.252 g HMF and 0.08 g malonic acid in 10 ml ethyl acetate was prepared in a pressure tube and 12 mg ethylenediamine on poly(styrene) was added as catalyst. The tube was placed in an oil bath that was heated to 80° C. After a reaction time of 1 h a conversion of 53% (aldehyde) was observed.

Example 8

A solution of 0.252 g HMF and 0.208 g malonic acid in 10 ml diethyl ether was prepared in a pressure tube and 12 mg ethylenediamine on poly(styrene) was added as catalyst. The tube was placed in an oil bath that was heated to 80° C. After a reaction time of 1 h a conversion of 52% (aldehyde) was observed.

Example 9

A solution of 0.252 g HMF and 0.208 g malonic acid in 10 ml isopropanol was prepared in a pressure tube and 12 mg ethylenediamine on poly(styrene) was added as catalyst. The tube was placed in an oil bath that was heated to 80° C. After a reaction time of 1 h a conversion of 54% (aldehyde) was observed.

Example 10

A solution of 0.252 g HMF and 0.208 g malonic acid in 10 ml THF was prepared in a pressure tube and 12 mg ethylenediamine on poly(styrene) was added as catalyst. The tube was placed in an oil bath that was heated to 80° C. After a reaction time of 5 h a conversion of 69% (aldehyde) was observed.

Example 11

A solution of 0.192 g furfural and 0.208 g malonic acid in 10 ml isopropanol was prepared in a pressure tube and 12 mg ethylenediamine on poly(styrene) was added as catalyst. The tube was placed in an oil bath that was heated to 80° C. After a reaction time of 1 h a conversion of 42% (aldehyde) was observed.

Example 12

A solution of 0.192 g furfural and 0.208 g malonic acid in 10 ml ethyl acetate was prepared in a pressure tube and 12 mg ethylenediamine on poly(styrene) was added as catalyst. The tube was placed in an oil bath that was heated to 80° C. After a reaction time of 1 h a conversion of 41% (aldehyde) was observed.

Example 13

A solution of 0.192 g furfural and 0.208 g malonic acid in 10 ml THF was prepared in a pressure tube and 12 mg ethylenediamine on poly(styrene) was added as catalyst. The tube was placed in an oil bath that was heated to 80° C. After a reaction time of 1 h a conversion of 40% (aldehyde) was observed.

Example 14

A solution of 0.252 g HMF and 0.208 g malonic acid in 10 ml THF was prepared in a 2 two-neck flask with a reflux condenser and 12 mg ethylenediamine on poly(styrene) was added as catalyst. The flask was placed in an oil bath that was heated to 70° C. After a reaction time of 5 h a conversion of 71% (aldehyde) was observed.

Example 15

A solution of 0.252 g HMF and 0.208 g malonic acid in 10 ml THF was prepared in a pressure tube and 12 mg ethylenediamine on poly(styrene) was added as catalyst. The tube was placed in an oil bath that was heated to 80° C. After a reaction time of 5 h a conversion of 62% (aldehyde) was observed.

Example 16

A solution of 0.48 g furfural and 0.520 g malonic acid in 25 ml THF was prepared in a two-neck flask and 30 mg ethylenediamine on poly(styrene) was added as catalyst. The flask was placed in an oil bath that was heated to 80° C. After a reaction time of 5 h a conversion of 65% (aldehyde) was observed.

Example 17

A solution of 0.64 g HMF and 0.502 g malonic acid in 25 ml THF was prepared in a two-neck flask and 30 mg ethylenediamine on poly(styrene) was added as catalyst. The flask was placed in an oil bath that was heated to 80° C. After a reaction time of 5 h a conversion of 79% (aldehyde) was observed.

Example 18

A solution of 0.96 g furfural and 1.04 g malonic acid in 10 ml THF was prepared in a pressure tube and 18 mg homogeneous ethylenediamine was added as catalyst. The tube was placed in an oil bath that was heated to 70° C. After a reaction time of 4 h a conversion of 89±4% (aldehyde) was observed.

Example 19

A solution of 0.196 g furfural and 0.208 g malonic acid in 10 ml THF was prepared in a three-neck flask and 12 mg ethylenediamine on poly(styrene) was added as catalyst. The flask was placed in an oil bath that was heated to 70° C. After a reaction time of 4 h a conversion of 43% (aldehyde) was observed.

Example 20

A solution of 0.196 g furfural and 0.208 g malonic acid in 10 ml THF was prepared in a pressure tube and 10 mg ethylenediamine on poly(styrene) was added as catalyst. The tube was placed in an oil bath that was heated to 70° C. After a reaction time of 4 h a conversion of 53% (aldehyde) was observed.

Example 21

A solution of 0.252 g HMF and 0.208 g malonic acid in 10 ml THF was prepared in a three-neck flask and 10 mg ethylenediamine on poly(styrene) was added as catalyst. The flask was placed in an oil bath that was heated to 80° C. After a reaction time of 10 h a conversion of 90% (aidehyde) was observed.

Example 22

A solution of 0.252 g HMF and 0.208 g malonic acid in 10 ml THF (with BHT inhibitor) was prepared in a pressure tube and 20 mg ethylenediamine on poly(styrene) was added as catalyst. The tube was placed in an oil bath that was heated to 80° C. After a reaction time of 5 h a conversion of 70% (aldehyde) was observed.

Example 23

A solution of 0.252 g HMF and 0.208 g malonic acid in 10 ml THF (with BHT inhibitor) was prepared in a pressure tube and 30 mg ethylenediamine on polystyrene) was added as catalyst. The tube was placed in an oil bath that was heated to 80° C. After a reaction time of 5 h a conversion of 86% (aldehyde) was observed.

Example 24

A solution of 0.252 g HMF and 0.208 g malonic acid in 10 ml THF (with BHT inhibitor) was prepared in a pressure tube and 40 mg ethylenediamine on poly(styrene) was added as catalyst. The tube was placed in an oil bath that was heated to 80° C. After a reaction time of 5 h a conversion of 90% (aldehyde) was observed in several experiments.

Example 25

A solution of 0.252 g HMF and 0.123 g malononitrile in 10 ml THF (with BHT inhibitor) was prepared in a pressure tube and 10 mg ethylenediamine on poly(styrene) was added as catalyst. The tube was placed in an oil bath that was heated to 80° C. After a reaction time of 5 h a conversion of 96% (aldehyde) was observed.

Example 26

A solution of 0.196 g furfural and 0.123 g malononitrile in 10 ml THF (with BHT inhibitor) was prepared in a pressure tube and 10 mg ethylenediamine on poly(styrene) was added as catalyst. The tube was placed in an oil bath that was heated to 80° C. After a reaction time of 5 h a conversion of 95% (aldehyde) was observed.

Example 27

A solution of 0.196 g furfural and 0.123 g malonic acid in 10 ml THF (with BHT inhibitor) was prepared in a pressure tube and 10 mg magnesium oxide was added as catalyst. The tube was placed in an oil bath that was heated to 80° C. After a reaction time of 5 h a conversion of 10% (aldehyde) was observed. The relatively low observed conversion could possible be due to the deactivation of the catalyst.

Example 28

A solution of 0.252 g HMF and 0.123 g malononitrile in 10 ml THF (with BUT inhibitor) was prepared in a pressure tube and 2 μl ethylenediamine (homogeneous) was added as catalyst. The tube was placed in an oil bath that was heated to 80° C. After a reaction time of 5 h a conversion of 99% (aldehyde) was observed.

Example 29

The conversion of biomass may result in mixtures of pentoses and hexoses that can possibly be dehydrated to furfural and hydroxymethylfurfural (HMF), respectively. The Knoevenagel reaction for mixtures of the two aldehydes was investigated by preparing a solution of 0.252 g HMF, 0196 g furfural, and 0.208 g malonic acid in 10 ml THF in a pressure tube. Twelve mg ethylenediamine on poly(styrene) was added as catalyst. The tube was placed in an oil bath that was heated to 70° C. After a reaction time of 1 h a conversion of 20±1 and 19±1% was observed for HMF and furfural, respectively.

Example 30

A solution of 0.252 g HMF and 0.208 g malonic acid in 10 ml THF was prepared in a pressure tube and 10 mg ethylenediamine on poly(styrene) was added as catalyst. The tube was placed in an oil bath that was heated to 70° C. After a reaction time of 5 h a conversion of 64±5% (aldehyde) was observed with a selectivity for the di-acid of 99%. The decarboxylated HMF product was identified with a selectivity of 1%.

Example 31

A solution of 0.196 g furfural and 0.208 g malonic acid in 10 ml THF was prepared in a pressure tube and 10 mg ethylenediamine on poly(styrene) was added as catalyst. The tube was placed in an oil bath that was heated to 80° C. After a reaction time of 5 h a conversion of 50% (aldehyde) was observed with a selectivity for the di-acid of 95%. The decarboxylated furfural product was identified with a selectivity of 5%.

Example 32

A solution of 0.196 g furfural and 0.208 g malonic acid in 10 ml THF was prepared in a pressure tube and 30 mg 3-aminopropyl on silica was added as catalyst. The tube was placed in an oil bath that was heated to 70° C. After a reaction time of 5 h a conversion of 53% (aldehyde) was observed with a selectivity for the di-acid of 99%.

Example 33

A solution of 2 mmol (0.252 g) HMF and 2 mmol (0.208 g) malonic acid in 10 ml ethyl ether or 10 ml ethyl acetate was prepared and 10 mg of ethylenediamine on poly(styrene) was added as catalyst. The mixture was heated to 80° C. for 5 hours. In both cases, the solid product 2-((5-(hydroxymethyl) furan-2-yl)methylene)malonic acid precipitated out of the solution in approximately 50% yield and 99% selectivity.

Example 34

Figure 3:
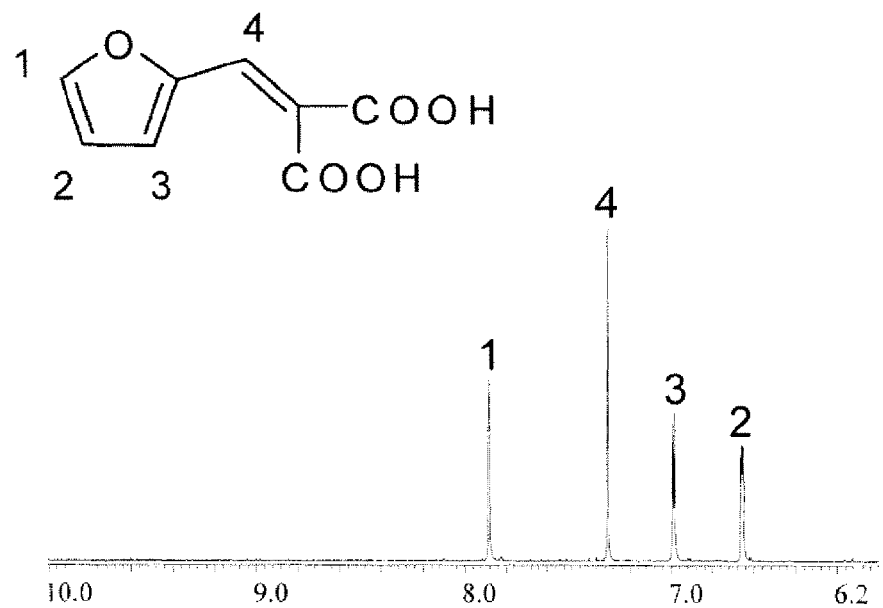
FIG. 3 shows an $^1H$ NMR spectrum of a product mixture resulting from one embodiment of the instant invention.
Figure 4:
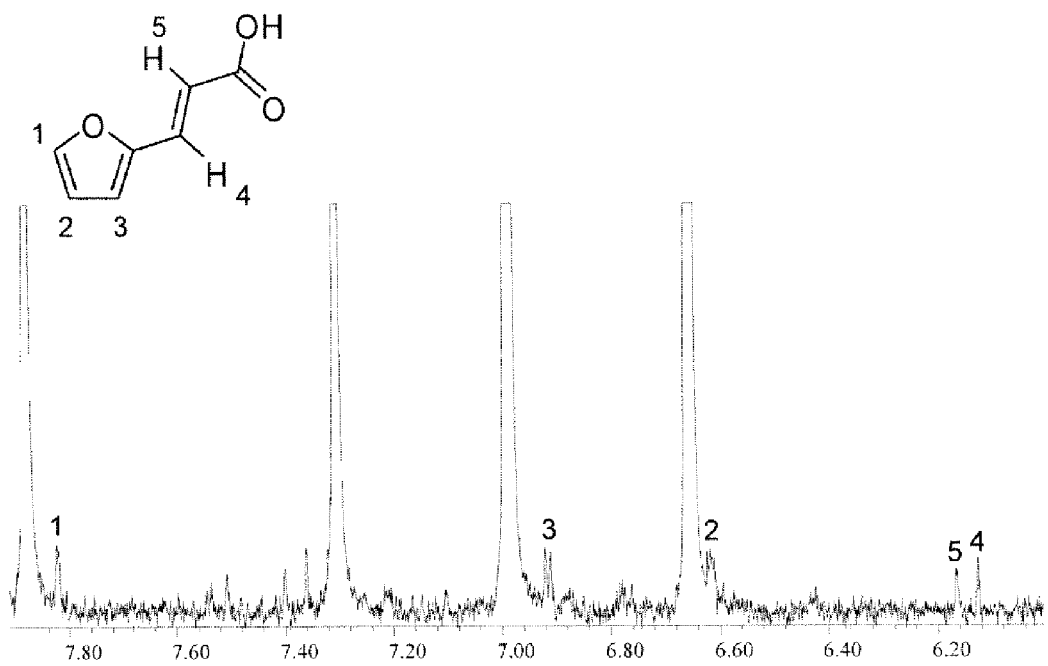
FIG. 4 shows an $^1H$ NMR spectrum of a product mixture resulting from one embodiment of the instant invention.
Figure 5:
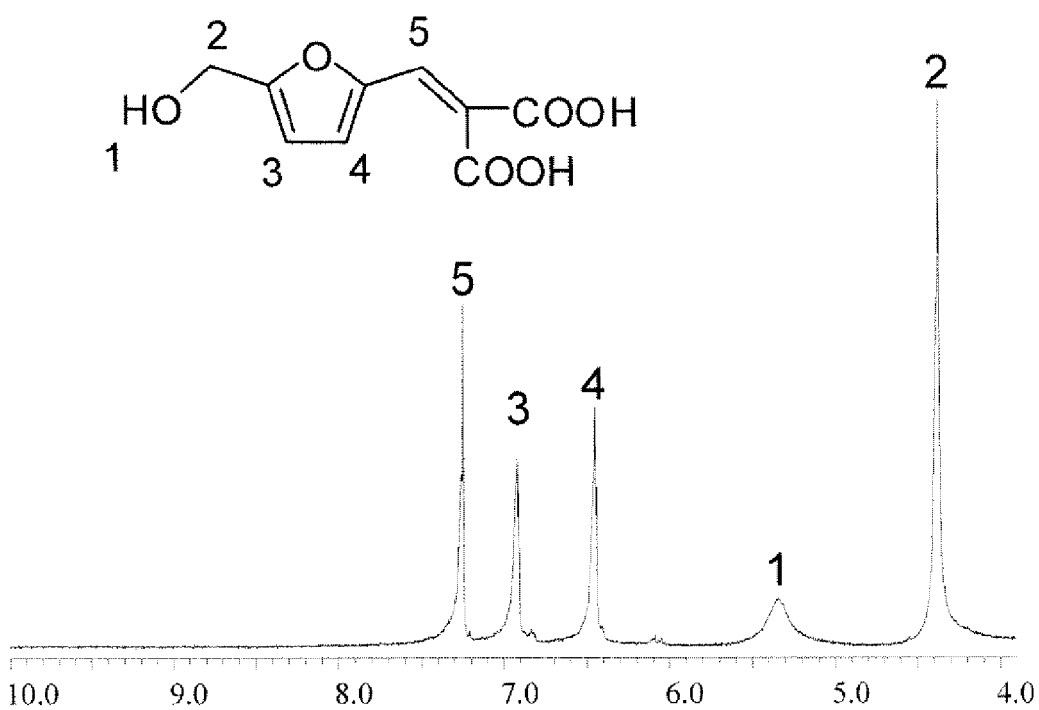
FIG. 5 shows an $^1H$ NMR spectrum of a product mixture resulting from one embodiment of the instant invention.
Figure 6:
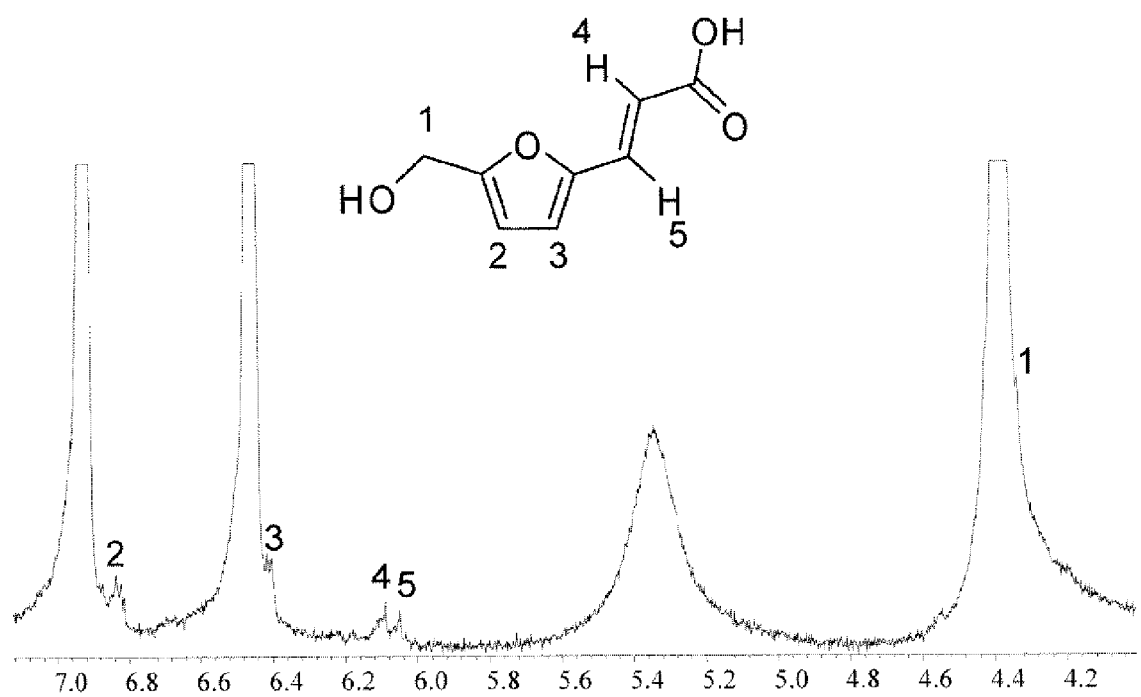
FIG. 6 shows an $^1H$ NMR spectrum of a product mixture resulting from one embodiment of the instant invention.

Samples of the product of some of the above examples were analyzed by NMR. FIG. 3 shows the relevant part of the $^1$H NMR spectrum of the product mixture of the reaction between furfural and malonic acid over 3-aminopropyl on SBA-15 and FIG. 4 shows the relevant part of the spectrum of the product mixture of the reaction between HMF and malonic acid with homogeneous ethylenediamine. In FIGS. 3 and 4, the main resonances are assigned to the protons of the primary product, which are formed by the reaction. In FIG. 3, the resonance corresponding to the aldehyde group in furfural (9.7 ppm) was only observed at extreme magnification. A conversion of 99% was calculated. All other resonances hardly exceeded the noise. The only other side reaction products identified are the unsubstituted monocarboxylic acids (UMA). FIGS. 5 and 6 show the UMA products for both furfural and HMF. This illustrates that potential side reactions, such as decarboxylation or aldol condensation, did not occur to a significant extent under the example conditions.

All publications and patent applications mentioned in this specification are herein incorporated by reference to the sane extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for enhancing molecular mass of biomass reactants comprising:
    a) forming a substituted or unsubstituted furfural from a biomass;
    b) reacting the substituted or unsubstituted furfural with an activated methylene compound comprising at least one electron withdrawing group in the presence of a catalyst to form a Knoevenagel product comprising a substituted furan compound comprising one or more electron-withdrawing groups and one or more carbon-carbon double bonds;
    wherein the activated methylene compound comprising at least one electron withdrawing group is selected from the group consisting of malononitrile, substituted or unsubstituted malonic acid or esters thereof, substituted or unsubstituted levulinic acid or esters thereof, and mixtures thereof, and
    c) hydrodeoxygenating the substituted or unsubstituted furan compound comprising one or more electron-withdrawing groups, or
        hydrodenitrogenating the substituted or unsubstituted furan compound comprising one or more electron-withdrawing groups, or
        hydrodeoxygenating and hydrodenitrogenating the substituted or unsubstituted furan compound comprising one or more electron-withdrawing groups.

2. The process of claim 1 which further comprises hydrodenitrogenating the substituted or unsubstituted furan compound comprising one or more electron-withdrawing groups.

3. The process of claim 1 which further comprises hydrodeoxygenating and hydrodenitrogenating the substituted or unsubstituted furan compound comprising one or more electron-withdrawing groups.

4. The process of claim 1, wherein the biomass is lignocellulosic.

5. The process of claim 4, wherein the biomass comprises carbohydrates.

6. The process of claim 5, wherein the carbohydrates of the biomass comprise cellulose, hemicellulose, poly(aromatics), extractives, ash, or a mixture thereof.

7. The process of claim 1, wherein the substituted or unsubstituted furfural is formed from a biomass comprising greater than 50 percent carbohydrates.

8. The process of claim 1 wherein the furfural is substituted furfural.

9. The process of claim 8 wherein the substituted furfural comprises 5-hydroxymethyl-furfural.

10. The process of claim 1 wherein the activated methylene compound comprising at least one electron withdrawing group is selected from the group consisting of a methyl ester of substituted or unsubstituted malonic acid, an ethyl ester of substituted or unsubstituted malonic acid, and mixtures thereof.

11. The process of claim 1 wherein the catalyst is a solid base.

12. The process of claim 1 wherein the catalyst is a supported organic base.

13. The process of claim 1 wherein the catalyst comprises a catalyst selected from the group consisting of ethylenediamine on poly(styrene), 3-aminopropyl-functionalized silica or other base-functionalized oxide materials, dimethylaminopyridine on poly(styrene), MgO, hydrotalcites, oxynitrides, alkali exchanged zeolites, and mixtures thereof.

14. The process of claim 1 wherein the reaction between substituted or unsubstituted furfural and activated methylene compound comprising at least one electron withdrawing group is conducted in the presence of a solvent.

15. The process of claim 14 wherein the solvent is selected from the group consisting of tetrahydrofuran (THF), ethyl acetate, diethyl ether, water, toluene, hexanes, isopropanol, and mixtures thereof.

16. The process of claim 1 wherein the reaction between substituted or unsubstituted furfural and activated methylene compound comprising at least one electron withdrawing group is conducted in the absence of a solvent.

17. The process of claim 1 wherein the substituted or unsubstituted furan compound comprising one or more electron-withdrawing groups is 2-(furan-2-ylmethylene)malonic acid, 5-hydroxymethyl-2-(furan-2-ylmethylene)malonic acid, or a mixture thereof.

18. The process of claim 1 wherein the reaction between the substituted or unsubstituted furfural with an activated methylene compound is conducted at a temperature of greater than about 60° C.

19. The process of claim 1 wherein the hydrodeoxygenated product is characterized by one or more of the following characteristics: (1) a viscosity less than the Knoevenagel product of the process of claim 1; (2) an energy density greater than the Knoevenagel product of the process of claim 1; or (3) a stability greater than the Knoevenagel product of the process of claim 1.

20. The process of claim 1 wherein the hydrodenitrogenated product is characterized by one or more of the following characteristics: (1) a viscosity less than the Knoevenagel product of the process of claim 1; (2) an energy density greater than the Knoevenagel product of the process of claim 1; or (3) a stability greater than the Knoevenagel product of the process of claim 1.

21. A process for enhancing molecular mass of biomass reactants comprising:
   a) forming a substituted or unsubstituted aldehyde or ketone from a biomass;
   b) reacting the substituted or unsubstituted aldehyde or ketone with an activated methylene compound comprising at least one electron withdrawing group in the presence of a catalyst to form a substituted or unsubstituted Knoevenagel product; and
   c) reacting the substituted or unsubstituted Knoevenagel product with $H_2$ to form a product which is hydrodeoxygenated, hydrodenitrogenated, or both wherein the product which is hydrodeoxygenated, hydrodenitrogenated, or both comprises one or more branched alkenes, one or more branched alkanes, or a mixture thereof;
   wherein the activated methylene compound comprising at least one electron withdrawing group is selected from the group consisting of malononitrile, substituted or unsubstituted malonic acid or esters thereof, substituted or unsubstituted levulinic acid or esters thereof, and mixtures thereof.

22. The process of claim 21 wherein the substituted or unsubstituted aldehyde or ketone is reacted with the activated methylene compound comprising at least one electron withdrawing group in the presence of a solvent.

23. The process of claim 22 wherein the solvent is selected from the group consisting of tetrahydrofuran (THF), ethyl acetate, diethyl ether, water, toluene, hexanes, isopropanol, and mixtures thereof.

24. The process of claim 21 characterized by a conversion of greater than 40 percent based on the substituted or unsubstituted aldehyde or ketone.

25. The process of claim 21 wherein the product which is hydrodeoxygenated, hydrodenitrogenated, or both comprises at least one less oxygen atom than the substituted or unsubstituted Knoevenagel product.

26. The process of claim 21 wherein the process further comprises increasing the molecular weight of the product which is hydrodeoxygenated, hydrodenitrogenated, or both.

27. The process of claim 26 wherein the process further comprises hydrogenating the product after increasing its molecular weight.

* * * * *